United States Patent [19]

Fabrizi et al.

[11] Patent Number: 5,279,944
[45] Date of Patent: Jan. 18, 1994

[54] METHOD AND REAGENT COMPOSITION FOR THE DETERMINATION OF ALANINE AMINOTRASFERASE AND HBSAG ANTIGEN IN THE SAME BIOLOGICAL SPECIMEN

[75] Inventors: Paolo Fabrizi, Monteriggioni; Francesco Donnini, Arezzo; Alessandro Tabacco, Monteriggioni, all of Italy; Paolo Tarli, deceased, late of Monteriggioni, Italy, by: Piera Lelli Tarli, Giovanni Tarli, Lorenzo Tarli, heirs

[73] Assignee: Sclavo S.p.A., Siena, Italy

[21] Appl. No.: 700,611

[22] Filed: May 15, 1991

[30] Foreign Application Priority Data

May 18, 1990 [IT] Italy ................. 20377 A/90

[51] Int. Cl.$^5$ .......... C12Q 1/48; C12Q 1/26; C12Q 1/28
[52] U.S. Cl. .......................... 435/15; 435/4; 435/5; 435/7.1; 435/25; 435/28; 435/810; 436/820
[58] Field of Search .......... 435/4, 5, 7.1, 25.15, 435/28, 810; 436/820

[56] References Cited

U.S. PATENT DOCUMENTS

| | | | |
|---|---|---|---|
| 4,666,832 | 5/1987 | Elstner | 435/25 |
| 4,707,439 | 11/1987 | Seto | 435/5 |
| 4,778,757 | 10/1988 | Teshima | 435/28 |
| 4,818,688 | 4/1989 | Adamich | 435/7 |
| 4,870,026 | 9/1989 | Wands | 436/548 |
| 5,061,619 | 10/1991 | Wilson | 435/5 |

FOREIGN PATENT DOCUMENTS 0397424 11/1990 European Pat. Off. .

OTHER PUBLICATIONS

White, D. O. Medical Virology Academic Press Orlando 1986 pp. 371-373.
IFCC Methods for the Measurement of Catalytic Concentrations of Enzymes Part 3, IFCC Method for Alanine Aminotransferase (L-Alanine: 2-Oxoglutarate Aminotransferase, EC 2.6.1.2), prepared by H. U. Bergmeyer et al., from *Clinica Chimica Acta*, 105(1980) 147F-154F.

Primary Examiner—Michael G. Wityshyn
Assistant Examiner—Ralph Gitomer
Attorney, Agent, or Firm—Birch, Stewart, Kolasch & Birch

[57] ABSTRACT

The enzyme alanine aminotransferase (ALT) is colorimetrically determined as the hydrogen peroxide obtained in the pyruvate hydrolysis reaction catalysed by the enzyme pyruvate oxidase which develops a colour read at 550 nm making use of a reagent composition buffered at pH comprised within 7.0 and 7.5 containing L-alanine, ketoglutaric acid, a source of inorganic phosphorous, the enzyme pyruvate oxidase, a system for revealing the hydrogen peroxide and optionally one or more co-factors which interact in the enzymatic reaction catalysed by the enzyme pyruvate oxidase. It is moreover described a method for the determination of the enzyme alanine aminotransferase making use of said reagent composition and of the surface antigen of the hepatitis B virus (HBsAg), by enzyme-immune assay, in the same serum specimen and in the same well of a microtitration plate. The method is particularly useful for checking the suitability of the blood intended for transfusions since it can be easily carried out with equipments and instruments widely used for the immunoenzymatic screening of infectivity. Furthermore it enables to test in the same analytical assay the two labels of hepatocyte infections necessarily researched in the transfusion centres on biological specimens and to select among the donors the most likely candidates to transmission of the NANB hepatitis virus.

23 Claims, No Drawings

METHOD AND REAGENT COMPOSITION FOR THE DETERMINATION OF ALANINE AMINOTRASFERASE AND HBSAG ANTIGEN IN THE SAME BIOLOGICAL SPECIMEN

DESCRIPTION

The present invention relates, in general, to a method for the determination of the alanine aminotransferase (ALT) in a specimen of human serum and to a reagent composition for carrying out the same. In particular the present invention relates to a method for the determination of the enzyme alanine aminotransferase (ALT) making use of said reagent composition and of the hepatitis B virus surface antigen (HBsAg) by enzyme-linked immune test, in the same serum specimen and in the same well of a microtitration plate. The transfusion of homologous blood subjects the patient, in addition to the risks of immunological nature, also to the risk of many and often serious diseases due to infections like AIDS and posttransfusion hepatitis (EPT). Among these later, the infections from hepatitis B and NANB viruses are the most serious because of both incidence and prognosis. In particular, the EPT from NANB virus exhibits an incidence of about 10% of the patients submitted to transfusion of blood units and clotting factor concentrates. In about 20% of the cases, this infection develops into cirrhotic forms. The prevention of such pathological states is performed by means of a double screening comprising a) the exclusion of subjects as donors who to belong to categories at risk of infection and b) the exclusion of subjects classified as hepatitis carriers on the basis of specific direct (antigens) or indirect (antibodies) indicators or at least on the basis of indicators specific for the hepatic injury associated to the infection. As far as hepatitis B is concerned, the detection of infected carriers may effectively be carried out by means of assays for the presence of the surface antigen of hepatitis B virus (marker HBsAg). In particular, the research of HBsAg is effected making use of so-called third generation methods, like RIA (Radio Immuno Assay) based on the solid phase radioimmuno criteria and EIA (Enzyme Immuno Assay) based on immunoenzymatic criteria always on solid phase. In the case of NANB hepatitis, which represents 90% of EPT, the prevention of the transmission of a said virus is quite critical because of the lack of known small marker of NANB virus infection. Recently the likely aetiological agent of such an infection has been isolated and a part of the virion genome designated C (HCV) has been cloned; permitting the development of a serological test based on a HCV protein obtained by genetic engineering. However this new test is still under evaluation. Therefore, the control of donors capable of spreading the NANB virus is at present effected using nonspecific indicators of the infection as, for example, the enzyme alanine amino transferase (L-alanine-alpha-ketoglutarate aminotransferase) (ALT), which represents the indicator of the hepatocyte lysis by the NANB virus or another hepatotropic virus. The alanine aminotransferase, an enzyme located in the liver, catalyses the following reaction:

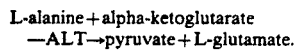

The clinical interest in determining the ALT in serum is mainly connected to the hepatic pathology. In fact many experimentations have put in evidence a clear correlation between the ALT level in donors and the occurrence of hepatitis NANB in receivers. Patients who received one single blood unit with ALT>0=45 Units/liter (U/l) showed a hepatitis incidence 4 times higher than that of patients transfused with blood units with lower concentrations in ALT. Moreover the transfusion of two blood units having the same titre (ALT>0=45 U/l) gave rise to NANB hepatitis in 91% of the cases. Therefore the selection of the donors on the basis of the ALT level should lead to a 40% decrease of NANB EPT. Also the anti-core antibodies (HBcAb) may be an indicator of NANB infections and recently the risk of contracting NANB hepatitis has been confirmed to be three times higher in patients receiving HBcAb positive blood (Bull. WHO 1988, 66 (4), 433–455). The presence of antibodies directed against the hepatitis B virus core antigen (anti-HBcAg), which gives evidence of the successful replication of the hepatitis B virus, increases indeed the likelihood that the subject may have been infected by other pathogens too, as NANB virus, which are transmitted parenterally. Thus the exclusion from blood donation of persons exhibiting an ALT value higher than 45 U/l decreases the NANB EPT occurrence by 40% and such a decrease may be brought to 60% by further carrying out the donor selection on the basis of the seronegativeness for anti HBcAg antibodies. For this reason the leading organisations for blood collection definitely require the determination of both ALT and anti HBcAg antibodies in donor blood. Generally the determination of ALT is carried out by colorimetric test (Reitman, S. and Frankel, E. (1957) Am. J. Clin. Pathol. 28, 56) or by UV test (ultraviolet) (IFCC, (1980), Clin. Chim. Acta, 105, 147 F). In particular the colorimetric determination of ALT is made directly as phenylhydrazon, which is the product developed by reacting in acid medium pyruvate with 2,4-dinitrophenylhydrazine, which gives, in alkaline medium, a dark brown colour monitored at 520–550 nm versus a blank and extrapolating the corresponding value of enzyme activity from a titration curve. The method is time-consuming (about 1 hour), it needs a lot of reagents, the preparation of a standard curve and analytical conditions (basic pH) which denature the complex of the anti-HBsAg antibodies immobilized upon the walls of microplate wells and the HBsAg. Furthermore a suboptimal amount of alpha-ketoglutaric acid is applied in the assay, since too high of an amount of this ketoacid would interfere with the final colorimetric reaction. The method ALT/UV, which is considered the preferred method vis-a-vis the aforementioned ALT colorimetric method, needs, in any case, for its development on microplate for enzyme-linked immuno-assay, the use of more sophisticated and expensive equipment than those generally available in nearly all the laboratories and suitable for determinations in the visible range only. For these reasons the analysis for determining ALT are generally carried out independently from those of HBsAg and of HBcAbs on serum specimens drawn from the same subject and, very frequently, in different laboratories. As it happens in the control of serum negativeness to markers of the most fearful transfusion diseases (AIDS and Hepatitis B), also the ALT determination in the same laboratory and on the same serum specimen is particularly advantageous and desirable. Therefore the object of the present invention is that of developing an easy, repeatable and economically convenient method for the detection of markers of hepatocyte infections (ALT and HBsAg) in the same human serum specimen. This object is achieved according to the present invention by applying for the determination of ALT a reagent composition which does not denature the complex, if any, between the anti HBsAg antibodies and the HBsAg; such a composition is capable of reducing the necessary incubation time before the monitoring, (the ALT / colorimetric method according to Reitman, S. needs 60 minutes) and it renders linear the hydrolysis reaction kinetic so improving the assay accuracy. In detail, the colorimetric determination of ALT is achieved as hydrogen peroxide released during the hydrolysis reaction of pyruvic acid catalysed in neutral medium by the enzyme pyruvate oxidase and developing a colour which can be read at 550 nm. Therefore an object of the present invention is represented by a method for the determination of the enzyme alanine aminotransferase and of the HBsAg antigen in the same serum specimen and in the same analytical session, wherein the enzyme alanine aminotransferase (ALT) is colorimetrically determined making use of a reagent composition at pH comprised within 7.0 and 7.5 containing L-alanine, ketoglutaric acid, an inorganic phosphorous compound, the enzyme pyruvate oxidase, a hydrogen peroxide indicator and optionally one or more co-factors which interact in the enzymatic reaction catalysed by the enzyme pyruvate oxidase. Further object of the present invention is a reagent composition suitable for the colorimetric determination of the enzyme alanine aminotransferase in a serum test comprising L-alanine, ketoglutaric acid, an inorganic phosphorous compound, the enzyme pyruvate oxidase, a hydrogen peroxide indicator and optionally one or more co-factors which interact in the enzymatic reaction catalysed by the enzyme pyruvate oxidase and having pH comprised within 7.0 and 7.5. A still further object of the present invention is a diagnostic kit for the determination of the enzyme alanine aminotransferase containing, in one or more separate receptacles, a composition comprising L-alanine, ketoglutaric acid, an inorganic phosphorous compound, the enzyme pyruvate oxidase, a hydrogen peroxide indicator and optionally one or more co-factors which interact in the enzymatic reaction and a buffer able to keep the pH values of the reagent composition within 7.0 and 7.5. Further objects of the present invention will be evident in the light of the disclosure and examples which follow. The reagent composition of the present invention may be in the form of a lyophilized to be reconstituted, before the use, in buffer capable of keeping the pH of the resulting reagent solution at a value comprised within 7.0 and 7.5, or in the form of reagent solution buffered at pH value comprised within 7.0 and 7.5. Any buffer compatible with the employed reagents may be used for the stated purpose. However, usually Tris-HCl at concentration comprised in the range 300–500 mmoles/liter is employed. Inorganic phosphorous compounds may be selected among those generally used as, for example $KH_2PO_4$ or $NaH_2PO_4$ in concentration of 1 to 2 mmoles/liter. Any co-factors of the enzymatic reaction catalysed by the enzyme pyruvate oxidase, compatible with the employed reagents, may be selected for this purpose.

Generally conventional co-factors are employed which are selected among thiamine pyrophosphate (TPP) in concentration of 1 to 5 mmoles/liter and/or inorganic salts of magnesium, manganese, calcium or cobalt in concentration 10 to 15 mmoles/liter. Magnesium inorganic salts, optionally added to the reagent composition for the stated purpose may be e.g. magnesium chloride or, preferably, magnesium chloride hexahydrate at concentration comprised within 10 and 15 mmoles/liter. Insofar as the indicator for hydrogen peroxide released from the enzymatic reaction of pyruvic acid and the enzyme pyruvate oxidase is concerned, this generally consists of a detector enzyme and a colourless specific substrate of the enzyme, which by positive sera, gives rise to a colourful reaction product. Enzymes suitable for the stated purpose can be selected from those able to reduce the hydrogen peroxide, as, for example, the peroxidase. A preferred reagent composition according to the present invention comprises:

| | |
|---|---|
| L-alanine | 500–800 mmoles/l |
| alpha-ketoglutaric acid | 15–18 mmoles/l |
| $KH_2PO_4$ | 1–2 mmoles/l |
| $MgCl_2 \cdot 6H_2O$ | 10–15 mmoles/l |
| thiamine pyrophosphate (TPP) | 1–5 mmoles/l |
| pyruvate oxidase (POP) | 3–5 U/ml |
| peroxidase (POD) | 2–3 U/ml |
| 4-aminoantipyrine (4-AAP) | 0.5–1 mmoles/l |
| dimethylaminobenzoic acid (DABA) | 2.5–5 mmoles/l |
| Tris-HCl buffer pH 7.35 | 400 mmoles/l |

The scheme of the detecting method for ALT, hereinafter designated ALT/VIS, which makes use of the aforementioned composition can be represented as follows:

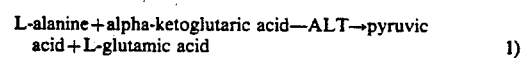

L-alanine + alpha-ketoglutaric acid —ALT→ pyruvic acid + L-glutamic acid    1)

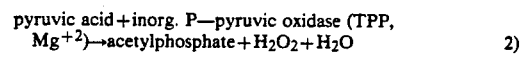

pyruvic acid + inorg. P—pyruvic oxidase (TPP, $Mg^{+2}$)→ acetylphosphate + $H_2O_2$ + $H_2O$    2)

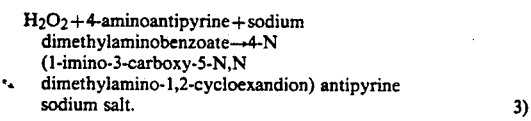

$H_2O_2$ + 4-aminoantipyrine + sodium dimethylaminobenzoate→4-N (1-imino-3-carboxy-5-N,N dimethylamino-1,2-cycloexandion) antipyrine sodium salt.    3)

The method of the present invention for the determination of ALT and HBsAg antigen in the same serum specimen comprises:

a) adsorbing the poly- or monoclonal anti-HBsAg antibodies upon the well walls of a microtitration plate at concentration comprised from 2 to 4 μg/well by incubating them firstly at temperature of, or about, 37° C. for a period of time of 1 to 3 hours thereafter at temperature of, or about, 4° C. for a period of time of 15 to 20 hours; b) adding the serum specimen under assay, optionally diluted, to the wells and incubating at temperature of, or about, 37° C. for a period of time necessary to bring to accomplishment the bonding reaction of the HBsAg antigens, if any in the serum, and the adsorbed antibodies; c) removing most of the serum under assay from the wells; d) adding the aforementioned reagent composition to the remaining amount of serum in each well and incubating at temperature of 25° C. to 37° C.; e) determining the difference in optic density (O.D.) per min. of the sera under test and of a positive control serum with ALT activity of 45 U/l by reading at 550 nm; f) removing the reaction mixture from each well and thoroughly washing with distilled water; g) giving a poly- or monoclonal anti-HBsAg antibody/peroxidase conjugate into each well and incubating at temperature of about 37° C. for the time necessary to bring to accomplishment the reaction h) adding to each well the same volume of a mixture (1:1, v/v) of hydrogen peroxide and specific chromogenic substrate and incubating for 30 minutes at room temperature (20° C.-25° C.); i) blocking the enzymatic reaction by addition of 1N sulphuric acid and determining the HBsAg antigen by spectrophotometrical reading at 450 nm versus a blank obtained by replacement of the serum under test by distilled water. In the practice the determination of ALT[steps d) and e)] in the method of the present invention is achieved by mixing a fresh human serum specimen with a volume (0.100 to 0.300 ml) of the above reported reagent composition and monitoring the optic density (O.D.) variation at 550 nm versus a positive control serum with ALT activity of 45 U/l, each minute, for a total of about 5 minutes incubation, at temperature of 25° C. to 37° C., preferably at about 37° C. Sera which show a delta O.D./min. <14, comprised within 15 and 17 and <17 are respectively considered as normal, doubtful or pathological. The method according to the present invention offers both the advantages of giving no interferences with the immunological determination of HBsAg (example 2) and of being easily performed; it needs indeed short execution times, 5 minutes versus 60 minutes necessary for the ALT colorimetric determination according to Reitman, S.; moreover the preparation of a titration curve is not necessary. Therefore the method of the present invention allows to introduce the ALT determination to any analysis centre and offers the advantage of effecting and completing the research, necessarily requested, of the two markers of hepatitis virus infections (HBsAg and ALT) in the same analytical session and employing the same equipments (diluters/dispensers and vertical photometers for the reading of microplates). The reagent composition used in the method of the present invention is preferably formulated as diagnostic kit comprising in one or more separate receptacles the reagent composition and the buffer. More preferably the diagnostic kit of the present invention will contain two separate receptacles, the former comprising the buffer solution, the later the powdery reagent composition. A kit for the determination of the alanine aminotransferase (n° 91 assays) consists of a vial of powder A) containing:

| L-alanine | 10.00 mmoles |
|---|---|
| alpha-ketoglutaric acid | 0.300 mmoles |
| KH$_2$PO$_4$ | 0.020 mmoles |
| MgCl$_2$ * 6H$_2$O | 0.200 mmoles |
| thiamine pyrophosphate (TPP) | 0.020 mmoles |
| pyruvate oxidase (POP) | 60 U/ml |
| peroxidase (POD) | 50 U/ml |
| 4-aminoantipyrine (4-AAP) | 0.015 mmoles |
| dimethylaminobenzoic acid (DABA) | 0.075 mmoles | and of a vial of diluting solution B) containing Tris-HCl buffer pH 7.35 400 mmoles/l. For purpose of determination of alanine aminotransferase according to the method of the present invention the powder A) is reconstituted in the vial with 20 ml diluting solution. An amount of 0.2 ml of the so prepared reagent is collected and mixed with 0.020 ml (20 μl) fresh human serum. After 5 and 10 minutes incubation at 37° C., the difference in optic density at 550 nm is monitored versus a control blank obtained by replacing the serum with 0.020 ml distilled water. Furthermore the kit may comprise separately the reagents for the enzyme-linked immuno determination of HBsAg antigen in human serum. The following experimental examples are intended to illustrate, not to limit, the invention.

EXAMPLE 1

DETERMINATION OF ALT BY COLORIMETRIC ALT/VIS METHOD

The activity of the enzyme alanine aminotransferase is assayed on undiluted serum specimens in a 96 flat-bottomed well plate (Eflab-Oy) by colorimetric method making use of the composition of the present invention. Practically, after having dispensed 0.020 ml undiluted serum in each well of the microplate, a solution preincubated for 5-10 minutes at 37° C. and comprising the following constituents are added:

| L-alanine | 500 mM |
|---|---|
| alpha-ketoglutaric acid | 15 mM |
| KH$_2$PO$_4$ | 1 mM |
| MgCl$_2$ * 6H$_2$O | 10 mM |
| thiamine pyrophosphate (TPP) | 1 mM |
| pyruvate oxidase (POP) | 3 U/ml |
| peroxidase (POD) | 2-3 U/ml |
| 4-aminoantipyrine (4-AAP) | 0.5-1 mM |
| dimethylaminobenzoic acid (DABA) | 2.5-5 mM |
| Tris-HCl buffer pH 7.35 | 400 mM |

The plate is maintained at 37° C. for 5 minutes. At the end of the incubation a kinetic is effected at 37° C. for 5 minutes by monitoring the specimens at 550 nm in a vertical microplate scanner (EAR-400-SLT). The delta optic density (O.D.) per minutes is then calculated for the sera under test and for a control serum having ALT activity 45 U/l (threshold serum). Sera which show a delta O.D./min. <14, comprised within 15 and 17 and >17 are respectively considered as normal, doubtful or pathological.

EXAMPLE 2

Determination of the HBsAg antigen by ELISA assay and ELISA/ALT/VIS assay

Purpose of the experience is to check whether the combined performance of the HBsAg antigen determination by enzyme-linked immune method ELISA, and of ALT by colorimetric method with reading in the visible, modifies the analytical sensitivity of the test for the research of HBsAg. A pool of HBsAg positive sera diluted with negative serum (1:1, 1:3, 1:5, 1:7, 1:15 and 1:31) are analysed for the presence of the HBsAg antigen by enzyme-linked immune-assay ELISA, which comprises the following phases:

Phase 1: physical adsorption of poly- and monoclonal anti-HBsAg antibodies (concentration from 2 to 4 μg/well) upon the walls of flat-bottomed wells on a 96 well microtitration plate (Eflab-Oy) by incubating at 37° C. for 3 hours and at 4° C. for 16 hours.

Phase 2: Binding of the HBsAg antigen contained in 0.2 ml serum by incubation at 37° C. for 60 minutes to the antibodies adsorbed in the phase 1.

Phase 3: binding of the conjugate chimpanzee anti-HBsAg antibody/peroxidase to the HBsAg combined in the phase 2, by incubation at 37° C. for 60 minutes.

Phase 4: enzymatic reaction of the peroxidase on the conjugate combined in the phase 3 with 0.2 ml (1/1, v/v) mixture of hydrogen peroxide and tetramethylbenzidine chromogen for 30 minutes at room temperature (20°-25° C.).

Phase 5: block of the enzymatic reaction by adding 0.05 ml 1N sulphuric acid and monitoring the adsorbance by spectrophotometrical reading at 450 nm versus a blank consisting of the reaction mixture free of the specimen under test. The results reported in column 2 (ELISA HBsAg) of Table I show the positiveness of said sera. The same diluted sera are assayed for the presence of the HBsAg by the combined ELISA-/ALT/VIS method. Practically after execution of the phases 1 and 2 of the aforementioned ELISA assay, 0.180 ml (180 µl) of the serum comprised in each well are removed by suction (leaving a volume of 0.020 ml) and the determination of ALT is carried out according to example 1. Then, after removal by suction of the reaction mixture from any well and after completion of 5 washes with 0.4 ml distilled water/well, each for 4 seconds, the HBsAg determination is performed by ELISA assay as reported in phases 3, 4 and 5. The results, given as the ratio of the adsorption values of the diluted sera and the cutoff adsorption value (O.D.=0.150) are reported in column 3 of table I.

TABLE I

| Control serum dilutions | ELISA HBsAg | HBsAg/ALT/VIS |
| --- | --- | --- |
| 1:1 | 16.41 | 15.24 |
| 1:3 | 9.27 | 9.48 |
| 1:7 | 4.36 | 4.43 |
| 1:15 | 2.31 | 2.22 |
| 1:31 | 1.34 | 1.36 |

From table I it can be appreciated that the determination of ALT/VIS does not interfere with the enzyme-linked immuno determination of HBsAg.

EXAMPLE 3

Determination of ALT in serum specimens 48 sera, some of which had showed to be pathological as regard to the ALT activity previously determined with the UV method performed in cuvette according to Wroblewski, F. and La Due, J. (1956) Proc. Soc. Exp. Biol. Med., 91:569, were examined by the method ALT-UV on microplate (C) as reported in IFCC (1980) Clin. Chim. Acta, 105:147 F and by the combined method HBsAg/ALT/VIS (D).

The method (C) comprises the following phases:

Phase 1: to 0.020 ml (20 µl) undiluted serum maintained at 37° C. in a well of a microtitration plate, 0.250 ml (250 µl) of a monoreagent preincubated at 37° C. are added, which monoreagent was prepared upon reconstitution of a lyophilized in a volume of 0.1M Tris-HCl buffer, L-alanine 480 mM, pH 7.5 such as the final concentrations of the single constituents are the following: NADH (Böhringer)0.18 mM, LDH (lactic dehydrogenase) (Sigma) 2 U/ml, alpha-ketoglutaric acid 15 mM and L-alanine 20 mM. The plate is incubated for 5 minutes at 37° C.

Phase 2: At the end of the incubation a kinetics at 37° C. is effected for 5 minutes. The monitoring is carried out at 340 nm (ultraviolet) with a kinetic UV/VIS detector for microplates (Twin-Reader Plus from firm Flow). Thereafter the delta optic density (O.D.) per minute is calculated both for the sera under test and for a serum with an ALT activity of 45 U/l. The ALT enzymatic activity, given in international units (U), is calculated according to the following formula:

$$(O.D.)/min \times \text{calculus factor } (F) = U/l \ (37°C.)$$

$$F = \frac{Vt \times 1000}{Vc \times C.M.E \times P.O.} = 3445$$

where:

Vt is the total reaction volume (0.270 ml); 1000 is the conversion factor from ml to liter;

Vc is the specimen volume in the final reaction mixture;

C.M.E. is the NADH micromolar extinction coefficient at 340 nm (6.23 cm$^2$/mole);

P.O. is the vertical optic run in the well of the microplate (0.63 cm). Sera showing ALT values given in U/l respectively <50, comprised from 50 to 55 and >55 are correspondingly considered as normal, doubtful and pathological. At the same time the same undiluted sera are analysed by the combined method HBsAg/ALT/VIS as disclosed in example 2. Practically after achievement of the phase 1 and 2 of the ELISA assay, 200 µl reagent composition of example 1 preincubated at 37° C. are fed in each well to 20 µl undiluted serum. The plate is maintained at 37° C. for 5 minutes. At the end of the incubation a kinetics at 37° C. is performed for 5 minutes by reading the tests at 550 nm in a vertical detector for microplates (EAR-400-SLT). Then the delta optic density (O.D.) per minute is calculated both for the sera under test and for a control serum with an ALT activity of 45 U/l (threshold serum). Sera showing values of delta O.D./min<14, comprised from 15 to 17 and >17 are correspondingly considered as normal, doubtful and pathological. The results reported in table II hereinafter show a good consistency among the three methods and absence of interference by the HBsAg determination on the ALT test by means of colorimetric assay:

Method ALT/UV in tube: 18 normals (N), 5 doubtfuls (D) and 25 pathologicals (P);

Method HBsAg/ALT/VIS: 19 normals (N); 3 doubtfuls (D) and 26 pathologicals (P);

Method ALT/UV (C) 15 normals (N), 5 doubtfuls (D) and 28 pathologicals (P).

TABLE II

| | Test in tube | Tests on microplate | |
| --- | --- | --- | --- |
| Sera | automated (..O.D./min.-U/l) | ALT/UV (.O.D/min.-U/l) | HBsAg/ALT/VIS (.O.D/min.) |
| 1 | 11–24 N | 7–25 N | 10 N |
| 2 | 14–31 N | 8–27 N | 10 N |
| 3 | 10–21 N | 6–22 N | 8 N |
| 4 | 7–16 N | 5–18 N | 5 N |
| 5 | 7–15 N | 5–17 N | 5 N |
| 6 | 15–32 N | 10–33 N | 17 D |
| 7 | 12–26 N | 8–27 N | 12 N |
| 8 | 11–24 N | 7–25 N | 6 N |
| 9 | 11–28 N | 8–27 N | 11 N |
| 10 | 10–23 N | 6–20 N | 15 D |
| 11 | 10–22 N | 6–19 N | 18 P |
| 12 | 8–1 N | 6–16 N | 5 N |
| 13 | 9–20 N | 6–22 N | 5 N |
| 14 | 12–26 N | 8–27 N | 10 N |
| 15 | 8–17 N | 5–18 N | 5 N |
| 16 | 11–25 N | 6–22 N | 8 N |
| 17 | 12–26 N | 9–30 N | 12 N |
| 18 | 4–8 N | 3–9 N | 7 n |
| 19 | 24–54 D | 15–52 D | 19 P |
| 20 | 28–61 P | 17–60 P | 25 P |
| 21 | 25–56 P | 16–57 P | 20 P |
| 22 | 26–58 P | 17–60 P | 22 P |
| 23 | 26–57 P | 16–57 P | 20 P |
| 24 | 23–51 D | 15–53 D | 15 D |
| 25 | 23–50 D | 14–48 N | 15 D |
| 26 | 25–55 D | 16–56 P | 18 P |
| 27 | 23–51 D | 15–53 D | 15 D |

TABLE II-continued

| | Test in tube automated | Tests on microplate | |
|---|---|---|---|
| Sera | (..O.D./min.-U/l) | ALT/UV (.O.D/min.-U/l) | HBsAg/ALT/VIS (.O.D/min.) |
| 28 | 25–56 P | 16–58 P | 18 P |
| 29 | 29–64 P | 18–62 P | 33 P |
| 30 | 27–60 P | 18–63 P | 31 P |
| 31 | 27–60 P | 18–62 P | 26 P |
| 32 | 35–78 P | 22–77 P | 32 P |
| 33 | 40–88 P | 24–83 P | 41 P |
| 34 | 42–92 P | 26–90 P | 33 P |
| 35 | 28–62 P | 17–61 P | 23 P |
| 36 | 28–63 P | 18–62 P | 22 P |
| 37 | 36–80 P | 24–84 P | 48 P |
| 28 | 32–70 P | 21–72 P | 38 P |
| 39 | 30–66 P | 20–68 P | 33 P |
| 40 | 35–78 P | 22–76 P | 36 P |
| 41 | 40–88 P | 31–92 P | 42 P |
| 42 | 34–76 P | 21–73 P | 30 P |
| 43 | 52–115 P | 35–121 P | 67 P |
| 44 | 62–136 P | 43–150 P | 105 P |
| 45 | 76–168 P | 47–163 P | 120 P |
| 46 | 136–300 P | 84–289 P | 225 P |
| 47 | 66–146 P | 40–140 P | 65 P |
| 48 | 67–148 P | 45–156 P | 70 P |

We claim:

1. A method for the determination of alanine aminotransferase and of the hepatitis B virus surface antigen (HBsAg) in the same specimen of human serum and in the same well of a microtitration plate comprising:
   a) adsorbing anti-HBsAg antibodies upon the well walls of a microtitration plate at concentrations from 2 to 4 μg/well by incubating them firstly at temperature of about 37° C. for a period of time of 1 to 3 hours and thereafter at temperature of about 4° C. for a period of time of 15 to 20 hours;
   b) adding said serum specimen into each well and incubating at a temperature of 37° C. for a period of time sufficient to bind said antibodies with any HBsAg antigens present in said serum specimen;
   c) removing most of said serum specimen from each well;
   d) adding a reagent composition for determination of alanine aminotransferase, comprising in effective amounts, L-alanine, ketoglutaric acid, an inorganic phosphorus compound selected from the group consisting of $KH_2PO_4$ and $NaH_2PO_4$, a hydrogen peroxide indicator, pyruvate oxidase and buffers to the remaining serum specimen in each well and incubating at a temperature from about 25° C. to 37° C.;
   e) determining the difference in optic density (O.D.) per minute of said serum specimen and of a positive control serum specimen with ALT activity of 45 U/l by spectrophotometrically reading at 550 nm;
   f) removing the reaction mixture from each well and thoroughly washing the wells with distilled water;
   g) adding an anti-HBsAg antibody/peroxidase conjugate to each well and incubating at temperature of about 37° C. for a period of time sufficient to react said conjugate with the bound antigens of step (a);
   h) adding to each well a volume of a mixture (1:1, V/V) of hydrogen peroxide and specific chromogenic substrate and incubating at room temperature;
   i) blocking the enzymatic reaction by addition of a volume of 1N sulfuric acid and determining the HBsAg antigen by spectrophotometrically reading at 450 nm versus a blank obtained by replacement of said serum by distilled water.

2. The method according to claim 1, wherein in the stage d) said reagent composition comprises buffers to maintain the pH from 7.0 to 7.5.

3. The method according to claim 2, wherein the buffer is Tris-HCL in concentrations from 300 to 500 mmoles/liter.

4. The method according to claim 2, wherein the inorganic phosphorous compound is selected from the group consisting of $KH_2PO_4$ and $NaH_2PO_4$ in a concentration from 1 to 2 mmoles/liter.

5. The method according to claim 2, wherein said reagent composition further comprises co-factors selected from the group consisting of thiamine pyrophosphate, in concentrations from 1 to 5 mmoles/liter and inorganic salts of magnesium, manganese, calcium and cobalt in concentrations from 10 to 15 mmoles/liter.

6. The method according to claim 5, wherein the inorganic magnesium salts are selected from the group consisting of magnesium chloride and magnesium chloride hexahydrate.

7. The method according to claim 2, wherein the hydrogen peroxide indicator comprises a detector enzyme capable of reducing the hydrogen peroxide in a concentration of 2 to 3 Units/ml and a colorless specific substrate of said detector enzyme.

8. The method according to claim 7, wherein said detector enzyme is peroxidase.

9. The method according to claim 2, wherein said reagent composition is buffered at a pH from 7.0 to 7.5 with Tris-HCl and contains effective amounts of L-alanine, ketoglutaric acid, $KH_2PO_4$, the enzyme pyruvate oxidase, magnesium chloride hexahydrate, thiamine pyrophosphate, peroxidase, 4-aminoantipyrine and dimethylaminobenzoic acid.

10. A reagent composition for the determination of alanine aminotransferase in a human serum specimen comprising effective amounts of L-alanine, ketoglutaric acid, an inorganic phosphorous compound, the enzyme pyruvate oxidase, a hydrogen peroxide indicator and a buffer able to maintain the pH of said reagent composition at a value from 7.0 to 7.5.

11. The reagent composition according to claim 10, wherein the inorganic phosphorous compound is selected from the group consisting of $KH_2PO_4$ and $NaH_2PO_4$ in a concentration from 1 to 2 mmoles/liter.

12. The reagent composition according to claim 10, further comprising at least one cofactor selected from the group consisting of thiamine pyrophosphate, in a concentration from 1 to 5 mmoles/liter and inorganic salts of magnesium, manganese, calcium and cobalt in concentrations from 10 to 15 mmoles/liter.

13. The reagent composition according to claim 12, wherein the inorganic magnesium salt is selected from the group consisting of magnesium chloride and magnesium chloride hexahydrate.

14. The reagent composition according to claim 10, wherein the hydrogen peroxide indicator comprises a detector enzyme capable of reducing the hydrogen peroxide, in a concentration of 2 to 3 Units/ml and a colorless specific substrate of said detector enzyme.

15. The reagent composition according to claim 14, wherein said detector enzyme is peroxidase.

16. The reagent composition according to claim 10, wherein the buffer is Tris-HCl in a concentration from 300 to 500 mmoles/liter.

17. The reagent composition according to claim 10, comprising effective amounts of L-alanine, ketoglutaric acid, $KH_2PO_4$, the enzyme pyruvate oxidase, magnesium chloride hexahydrate, thiamine pyrophosphate, peroxidase, 4-aminoantipyrine and dimethylaminobenzoic acid and buffered at pH 7.0–7.5 with Tris-HCl in a concentration from 300 to 500 mmoles/liter.

18. A diagnostic kit for the determination of alanine aminotransferase in a serum specimen comprising, in one or more separate receptacles, L-alanine, ketoglutaric acid, an inorganic phosphorous compound, the enzyme pyruvate oxidase, a hydrogen peroxide indicator and a buffer able to keep the pH values of the reagent composition within 7.0 and 7.5.

19. The diagnostic kit according to claim 18, containing in one or more separate receptacles reagents for ELISA detection of the HBsAg antigen, said reagents comprising poly and monoclonal anti-HBsAg antibodies, poly and monoclonal anti-HBsAg antibodies/peroxidase conjugate, hydrogen peroxide, specific chromogenic substrate and sulphuric acid.

20. The method according to claim 1 wherein the step a) HBsAg antibodies are selected from the group consisting of monoclonal and polyclonal antibodies.

21. The reagent composition according to claim 10, further comprising an effective amount of at least one co-factor selected from the group consisting of thiamine pyrophosphate and inorganic salts of magnesium, manganese, calcium and cobalt, which interacts in the enzymatic reaction catalyzed by the enzyme pyruvate oxidase.

22. The diagnostic kit according to claim 18, further comprising an effective amount of at least one co-factor selected from the group consisting of thiamine pyrophosphate and inorganic salts of magnesium, manganese, calcium and cobalt, which interacts in the enzymatic reaction catalyzed by the enzyme pyruvate oxidase.

23. A reagent composition for the determination of alanine aminotransferase in a human serum specimen comprising;

| | |
|---|---|
| L-alanine | 500–800 mmoles/l, |
| alpha-ketoglutaric acid | 15–18 mmoles/l, |
| $KH_2PO_4$ | 1–2 mmoles/l, |
| $MgCl_2 \cdot 6H_2O$ | 10–15 mmoles/l, |
| thiamine pyrophosphate | 1–15 mmoles/l, |
| pyruvate oxidase | 3–5 u/ml, |
| peroxidase | 2–3 u/ml, |
| 4-aminoantipyrine | 0.5–1 mmoles/l, |
| dimethylaminobenzoic acid | 2.5–5 mmole/l, and |
| Tris-HCl buffer | 400 mmoles. |

* * * * *